United States Patent [19]

Watanabe et al.

[11] Patent Number: 5,489,281
[45] Date of Patent: Feb. 6, 1996

[54] PROCESS FOR CONTROLLING PATHOGENS IN CONTAINER

[75] Inventors: Tyler Watanabe; Su I. Yum, both of Los Altos; Eun S. Lee, Redwood City; Ivan W. Chin, Belmont, all of Calif.

[73] Assignee: Alza Corporation, Palo Alto, Calif.

[21] Appl. No.: 818,304

[22] Filed: Jan. 8, 1992

Related U.S. Application Data

[62] Division of Ser. No. 643,298, Jan. 18, 1991, Pat. No. 5,176,665.

[51] Int. Cl.$^6$ .................................................. A61M 1/00
[52] U.S. Cl. .......................... 604/317; 604/326; 422/28; 422/41
[58] Field of Search .................... 604/317, 322, 604/326–328, 49, 403, 416, 318, 319; 128/769; 422/28, 41

[56] References Cited

U.S. PATENT DOCUMENTS

| | | | |
|---|---|---|---|
| 3,312,221 | 4/1967 | Overment | 604/323 |
| 3,468,471 | 9/1969 | Linder | 422/294 |
| 4,144,309 | 3/1979 | Langston et al. | 422/205 |
| 4,193,403 | 3/1980 | Langston et al. | 128/225 |
| 4,233,263 | 11/1980 | Shaeffer | 422/28 |
| 4,236,517 | 12/1980 | Langston et al. | 128/275 |
| 4,241,733 | 12/1980 | Langston et al. | 128/275 |
| 4,392,848 | 7/1983 | Lucas et al. | 604/265 |
| 4,417,892 | 11/1983 | Meisch | 604/326 |
| 4,418,038 | 11/1983 | Theeuwes | 422/37 |
| 4,445,889 | 5/1984 | Wong et al. | 604/49 |
| 4,455,145 | 6/1984 | Theeuwes | 604/892 |
| 4,460,367 | 7/1984 | Wong et al. | 604/890 |
| 4,464,258 | 8/1984 | Wong et al. | 210/205 |
| 4,505,703 | 3/1985 | Gale et al. | 604/317 |
| 4,529,398 | 7/1985 | Wong et al. | 604/49 |
| 4,601,880 | 7/1986 | Wong et al. | 422/28 |
| 4,723,950 | 2/1988 | Lee | 604/322 |
| 4,728,498 | 3/1988 | Theeuwes | 422/29 |
| 4,740,201 | 4/1988 | Theeuwes | 604/29 |
| 4,863,445 | 9/1989 | Mayhan et al. | 604/322 |

*Primary Examiner*—Randall L. Green
*Assistant Examiner*—P. Zuttarelli
*Attorney, Agent, or Firm*—Paul L. Sabatine; Jacqueline S. Larson; Felissa H. Cagan

[57] ABSTRACT

A process for delivering a biocide to a container comprising admitting a biocide delivery device through an exit port of a urine container where the device is sized for passage through the exit port is disclosed.

1 Claim, 10 Drawing Sheets

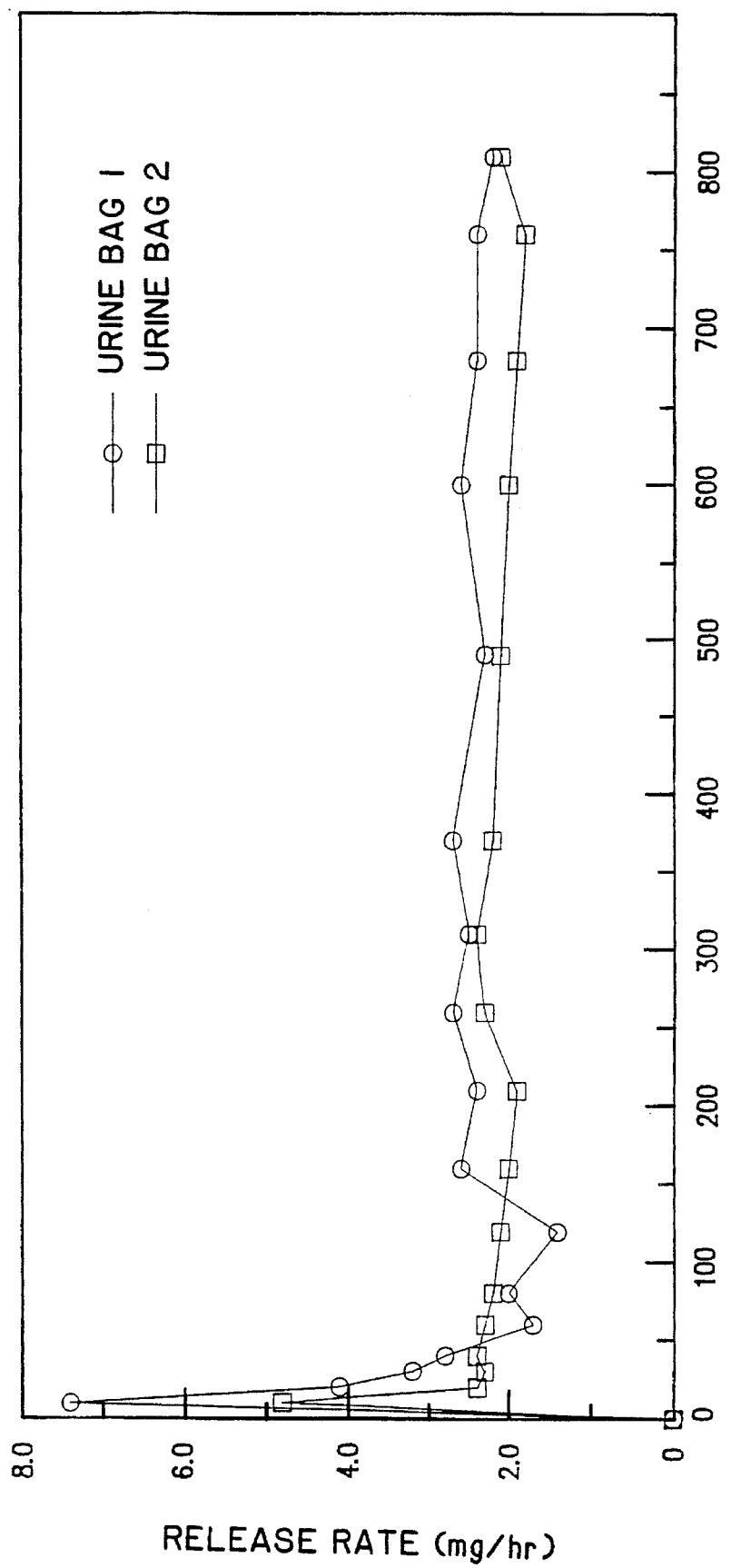

PROCESS FOR CONTROLLING PATHOGENS IN CONTAINER

This application is a division of U.S. Ser. No. 07/643,298 filed Jan. 18, 1991 which is now U.S. Pat. No. 5,176,665.

FIELD OF INVENTION

This invention pertains to an antimicrobial device adapted for passage through the drainage port of a urinary drainage container. This invention concerns also a patient-care system comprising, in combination, a urinary drainage container comprising a drainage port for inserting an antimicrobial device into the container, and an antimicrobial delivery device. The antimicrobial device delivers an agent into the container for preventing and eliminating unwanted pathogens inside the container. The invention relates also to a method for preventing and eliminating unwanted pathogens in a urine receiving container by inserting through the drainage exit into the container, a device for delivering an antimicrobial agent in the container.

BACKGROUND OF THE INVENTION

It is now generally acknowledged that indwelling catheterization in medical, surgical, gynecological, and urological patients often leads to serious infections of the urogenital tract. Indwelling urethral catheterization is performed in approximately 10 to 15 percent of hospitalized patients. Despite the use of the most careful aseptic technologies undertaken, while the catheter is in the patient, approximately fifty percent of the patients develop an infection, when a catheter is in place for twenty four hours or longer. Catheterization is harmful to the patient because (s)he is subjected to the risk of cystitis, acute pyelonephritis and life-threatening septicemia, which infections carry a risk of mortality, as reported in *Arch. Internal Med.*, Vol. 110, pp 703–11, (1962); *Antimicrob. Agents Chemother.*, pp 617–23, (1963); and Lancet, Vol. 1, pp 310–12 (1960).

The occurrence of the above-mentioned infections is encouraged by many circumstances. These circumstances include prolonged use of indwelling Foley catheters often accompanied by the absence of a sterile insertion and maintenance technique, and by having the catheter connected to a clean, but not sterile drainage collection container placed in the immediate vicinity of the patient's bed. These conditions and other circumstances predispose a patient to infection as reported in *Urinary Tract Infection and Its Management,* edited by Kaye, D., Chapter 15, "care of the Indwelling Catheter," pp 256–66, (1972), published by the C. V. Mosby Company, St. Louis, Mo..; and in "Factors Predisposing to Bacteriuria During Indwelling Urethral Catheterization," New Eng. J. Med., Vol. 291, pp 215–23, (1974).

The prior art noted attempts have been made to reduce the incidence of catheter acquired infections and to reduce the presence of unwanted organisms in drainage containers, but these attempts have not met with general acceptance. For example, one attempt consists in systemic chemoprophylaxis achieved by orally administering an antibiotic such as chloramphenicol, penicillin or streptomycin. This attempt, however, affords no significant protection against the acquisition after indwelling catheterization, as reported in *Arch. Internal Med.*, Vol. 110, pp 703–11, (1962); *Acta Chiv. Scand.*, Vol. 118, pp 45–52 (1959); and *Dis. Mon.*, pp 1–36, (Sept. 1960).

The medical and the patent literature are illustrative of attempts to eliminate the urinary drainage bag as a source of contamination leading to urinary tract infection. These attempts for preventing or substantially eliminating unwanted organisms include adding a biocide during manufacture to a drainage container, or placing a device inside the container wherein the device releases a biocide. For example, liquid formalin is added to the urine collection container for controlling, that is, killing pathogens. This method, however, does not enjoy general use because there is a risk of siphoning formalin into the urinary tract, as reported in *British Med. J.*, Vol. 2, pp 4233–25, (1964). In U.S. Pat. No. 4,233,263 the patentee Shaeffer disclosed adding 3% hydrogen peroxide solution to a urine bag for reducing the risk of urinary tract infection. This method is inherently subjected to poor results because of a lack of compliance. That is, each time urine is declined from the urinary drainage bag the hydrogen peroxide is drained and the solution must be reintroduced into the urine bag. This procedure requires mixing and agitation, and it is often accompanied by spilling of the solution. Also, hydrogen peroxide loses its strength over time.

The prior art, in U.S. Pat. Nos. 4,193,403 and 4,241,733 Langston et al discloses a device inside an urinary drainage bag. The device contains paraformaldehyde that depolymerizes to formaldehyde in the presence of moisture inside the urine drainage bag. While formaldehyde is an antimicrobial, it is not used because it may be injurious to an animal host. In U.S. Pat. No. 3,312,221 patentee overment discloses an urinary drainage bag having a porous plastic internal pouch containing an antimicrobial agent. The pouch is suspended so that incoming urine cascades over and through the pouch so that the antimicrobial agent will dissolve in the urine. However, an adequate dwell time of the antimicrobial agent in the urine is not assured by the quick flow process. Thus, the urine is undersatinated with antimicrobial agent with a high flow rate of urine into the urine container.

In view of the above presentation, it will be appreciated by those versed in the urinary drainage art, that a critical need exists for a novel and unique means for introducing an antimicrobial agent into an urinary container. The need exists for overcoming the difficulties associated with the prior art use of a preplaced delivery device inside the container, that exhaust itself of antimicrobial agent and is non-replaceable from outside with present, closed urinary drainage systems. It will thus be appreciated that a pressing need exists for a means that can be introduced into the container from outside the container for providing an antimicrobial agent in the container.

OBJECTS OF THE INVENTION

Accordingly, it is an immediate object of this invention to provide an improvement in urinary drainage collection, which improvement overcomes the disadvantages associated with the prior art.

Another object of this invention is to provide a drainage collection system comprising, in combination, a urine receiving container comprising means for receiving through its exit port a device that enters the container for delivering an antimicrobial agent for preventing the proliferation of and/or the elimination of pathogens in the container.

Another object of the invention is to provide an antimicrobial delivery device adopted for passage through the drainage port of a container for delivering an antimicrobial agent in the container.

Another object of the invention is to provide an urinary drainage container comprising a drainage container comprising a drainage port adapted for receiving a delivery device comprising dimensions corresponding to the dimensions of the drainage port for facilitating passage of the device into the container.

Another object of this invention is to provide a delivery device that is easily inserted through the drainage port of a urine receiving container for delivering an antimicrobial agent in the container, and which device embraces inventive simplicity, is inexpensive to make and is disposable.

Another object of the invention is to provide a delivery device for a drainage container, wherein the delivery device comprises a shape that corresponds to the internal shape of the drainage port of the container.

Another object of the invention is to provide a device for positioning inside a urinary drainage container through the drainage port of the container, and which device can be inserted at the beginning of a urine drainage program, or after the urine is drained from the container, once a day, twice a day or more often over any number of days.

Another object of the invention is to provide a delivery device that can comprise different antibacterial agents for killing bacteria in a urine receiving container, and which device can embrace any geometric shape adapted for pushing the device easily through the drainage port of the container.

These and other objects of the present invention will become more apparent upon a consideration of the drawings, the specification, and the accompanying claims.

BRIEF DESCRIPTION OF THE DRAWINGS

In the drawings, which are not drawn to scale, but are set forth to illustrate various embodiments of the invention, the drawing figures are as follows:

In FIG. 10, EVA denotes ethylene vinyl acetate copolymer and (40/60) denotes the device comprises 40 weight percent bronopol and 60 weight percent ethylene vinyl acetate copolymer;

FIG. 14 depicts a disinfectant released from two disinfectant delivery systems in urine bags comprising artificial urine substantially free of an added bacteria.

DETAILED DESCRIPTION OF THE DRAWINGS

Figure 1:
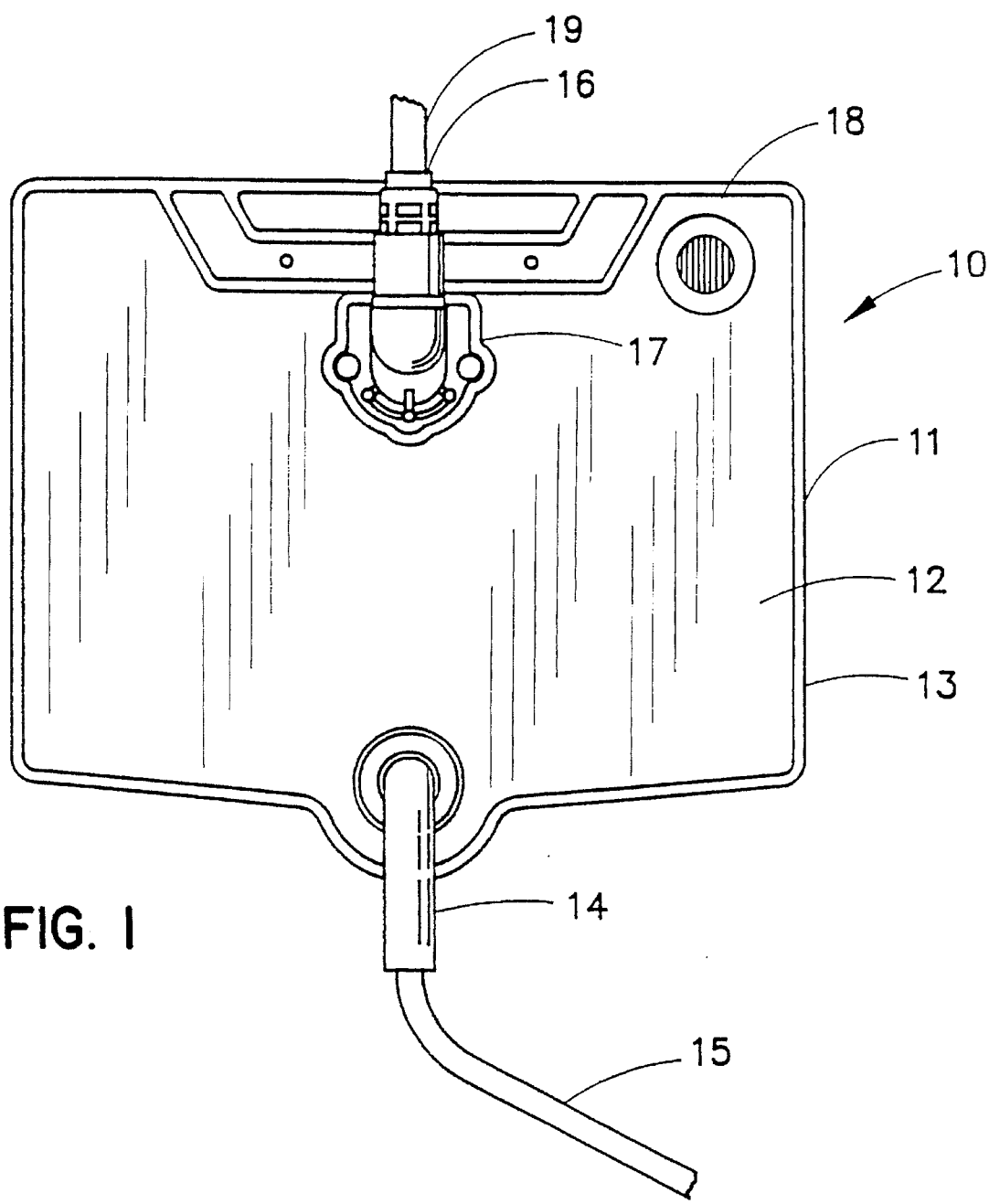
FIG. 1 is a fragmentary elevational view of a urine receptacle of the present invention comprising a drainage port adapted for inserting and antimicrobial agent dispensing device through the bottom of the receptacle into the receptacle.

Turning now to the drawings in detail, wherein the drawings are examples of various embodiments of the invention, and which examples are not to be construed as limiting the invention, one embodiment of an urinary drainage system is indicated in FIG. 1, by the numeral 10. In FIG. 1, urinary drainage system 10 comprises a container 11 comprising a front wall 12, and a back wall, not seen in FIG. 1. The front and back walls are made in one manufacture of a flexible, nontoxic plastic composition. The front wall and the back wall are joined around their peripheries 13 to define an internal chamber for receiving a fluid. Container 11 comprises a drainage port 14 for draining urine from the container. Drainage port 14 functions additionally as an entry passageway for pushing an antimicrobial dispensing device 15 into container 11. The antimicrobial dispensing device 15 dispenses an antimicrobial agent inside container 11 for substantially eliminating the presence of unwanted pathogens in container 11. Container 11 comprises a fluid entry port 16 designed for receiving an incoming tube for admitting fluid into container 11. Entry port 16 is connected to a connector 17 attached to front wall 12 of container 11. Container 11 optionally comprises a vent 18 on front wall 12. Vent 18 comprises a bacterial filter for preventing contamination from the atmosphere and for letting odors leave container 11. In use, a drainage tube 19, also identified as a catheter lets urine drain through the catheter from a patient into container 11, wherein dispensing device 15 delivers an antimicrobial agent for killing unwanted pathogens present in container 11.

Figure 2:
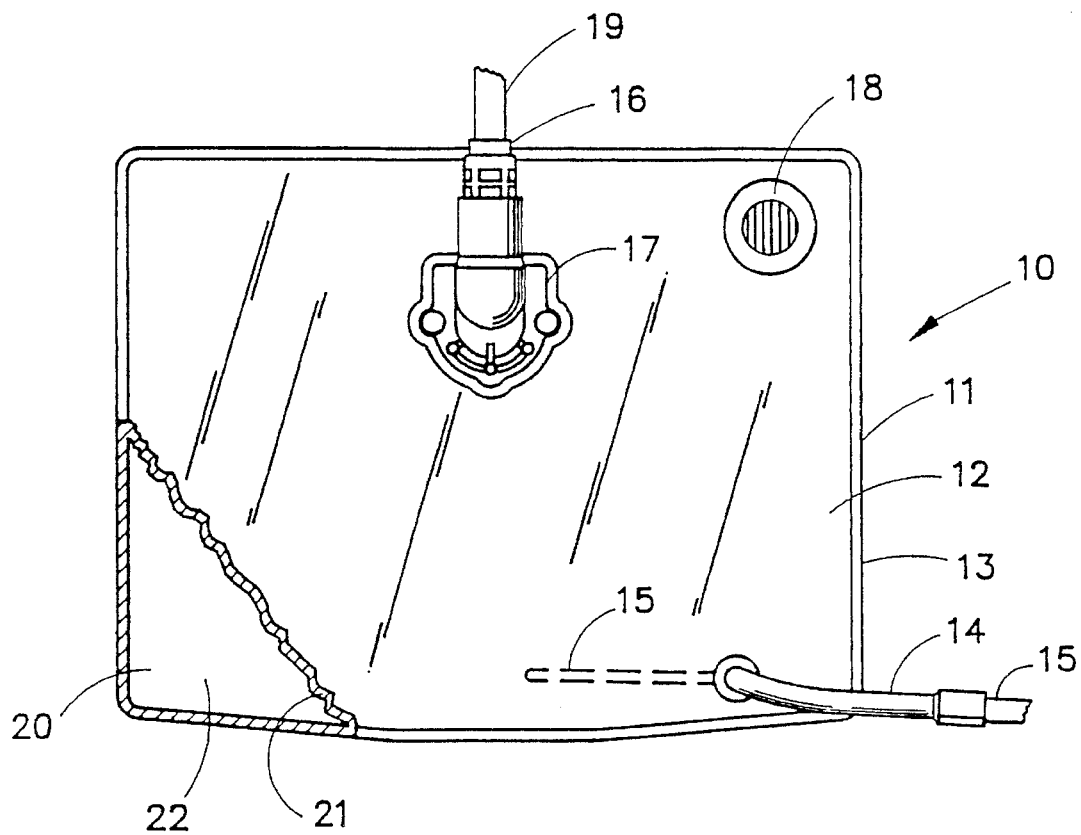
FIG. 2 is a fragmentary plain view, partly broken away for depicting the inside of a urine drainage container and for depicting a dispensing device entering the container through a bottom drainage port of the container.

Drawing FIG. 2 discloses another embodiment provided by the invention. In drawing FIG. 2, there is seen a urinary receiving container 11 comprising a front wall 12 and a back wall 20, seen at opened section 21. Front wall 12 and back wall 20 define an internal chamber 22 for receiving an incoming fluid. The front wall 12 and back wall 20 are joined around their peripheries 13, and in another manufacture container 11 can be extruded to define a container. In drawing FIG. 2, container 11 comprises a fluid entry port 16 for receiving incoming catheter 19. Entry port 16 connects to connector 17 suitably attached to front wall 12. Container 11 comprises a vent 18 comprising a bacterial filter to filter bacteria passing from the atmosphere into chamber 22 of container 11. Container 11 comprises a drainage port 14 for draining urine from the container and for pushing an antimicrobial dispensing device 15, seen in broken lines, in container 11.

Figure 3:
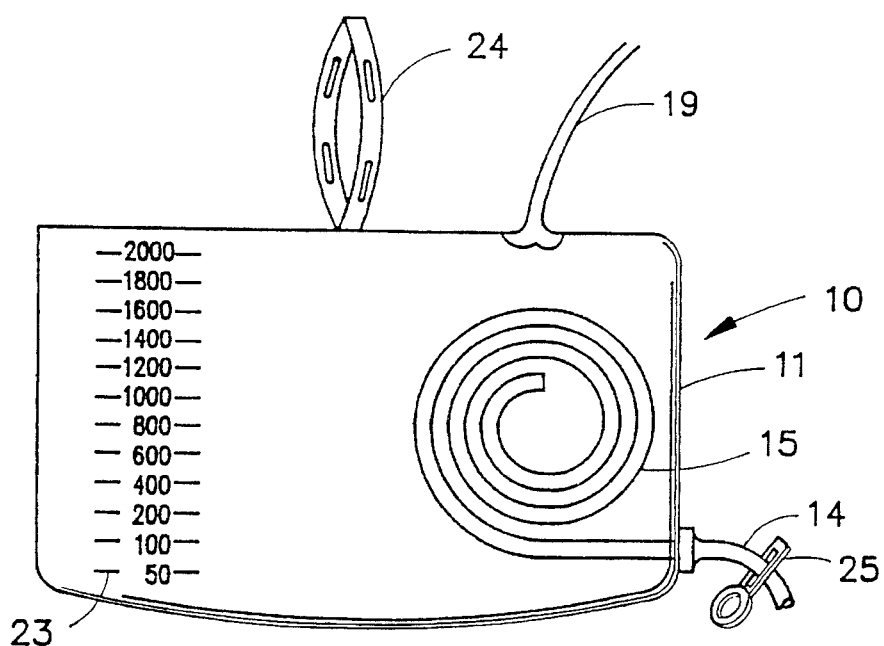
FIG. 3 illustrates a patient-care apparatus comprising a drainage container and an antimicrobial agent dispensing device in the container, which device was inserted through a bottom drainage port into the container.

Drawing FIG. 3 illustrates another embodiment of the invention comprising a patient care apparatus 10 manufactured with a volumetric scale 23 thereon for indicating the volume of fluid in container 11. In the embodiment depicted in FIG. 3, a dispensing device 15 is confined within container 11 for controlling the presence of pathogens in container 11. Device 15 controls the multiplication and precludes the survival of pathogens, or unwanted infectious organisms in container 11 by continually dispensing at a controlled rate an antibiotically effective amounts of an antimicrobial agent into container 11. Device 15 by dispensing an antimicrobial agent for the aseptic management of container 11, concomitantly inhibits and prevents the migration of infectious organisms into catheter 19. This inventive embodiment substantially prevents the development of catheter induced infections in a patient that are introduced through an indwelling catheter; which indwelling catheter passes through the urethra into the bladder, and drains the bladder through the catheter tubing connected to fluid drainage receptacle 11. In drawing FIG. 3, dispensing device 15 is introduced through flexible outlet port 14 for draining container 11. Outlet port 14 is equipped with a pinch clamp 25 for draining fluid from container 11. In drawing FIG. 3, apparatus 10 is made with a handle 24 for hanging container 11 from a stand placed in the vicinity of a patient's bed.

Figure 4:
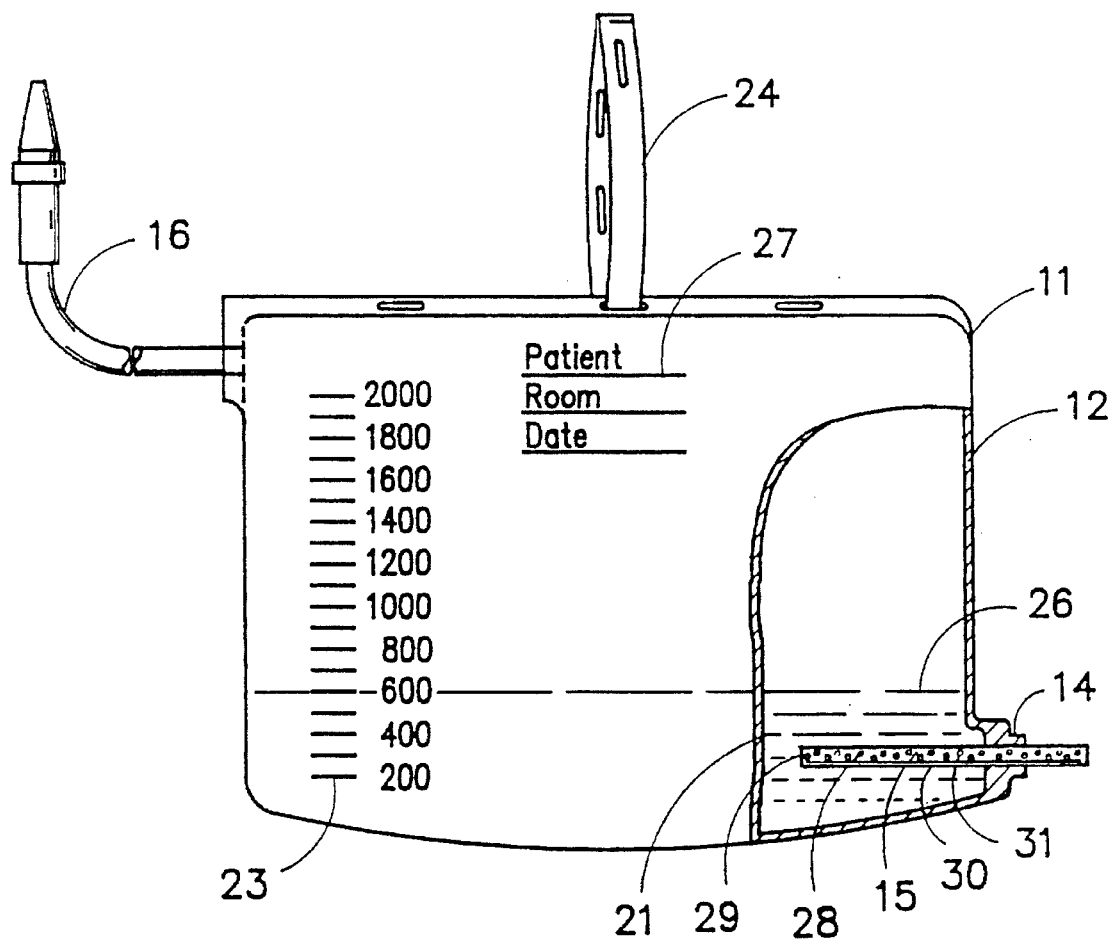
FIG. 4 is a view of another embodiment of the invention illustrating a receptacle in opened section housing a dispensing device in urine, wherein the device was inserted through the exit drainage port of the receptacle.

Drawing FIG. 4 depicts another patient-care apparatus 10 provided by the invention. In drawing FIG. 4, patient-care apparatus comprises a receptacle 11 that is a container for receiving and storing a biological fluid 26. Receptacle 11 has both a volumetric scale 23 thereon for indicating the volume of fluid in receptacle 11, and a patient identification area for indicating the origin of the biological fluid. Receptacle 11 of FIG. 4 is made with a front wall 12 with a section removed for illustrating its back wall 21. Front wall 12 and back wall 21 are made from a pair of thin, flat flexible plastic sheets such is polyethylene, polypropylene, and the like. In one preferred manufacture, front wall 12 is made from a transparent plastic such is plasticized polyvinyl chloride, and rear wall 21 is made of an opaque plastic such as polyvinyl chloride containing titanium dioxide. In this embodiment, the internal contents are visible as wall 12 and wall 21 arranged back-to-back against each other highlight the internal contents of receptacle 11.

Receptacle 11 comprises an inlet means 16 for receiving an incoming catheter that established fluid communication between the interior and the exterior of receptacle 11. Receptacle 11 comprises an outlet port 14 positioned at the bottom of receptacle 11 distant from inlet 16. In antimicrobial dispensing device 15 is passed through inlet port 14 into container 11 wherein the delivery device releases controlled and needed amounts of an antimicrobial agent into urine 26 for killing pathogens in urine 26. A hanging strap 24 is suitably attached to receptacle 11 for hanging receptacle 11 in a fluid receiving position at the bedside of a catheterized patient.

Delivery device 15 as used for the purpose of this invention dispenses an antimicrobial agent for producing an antiseptic environment. The term antimicrobial, as used herein, includes biocide, and means an agent that destroys, inhibits, and prevents the growth of pathogens, the propagation, multiplication, and the like of unwanted organisms. The term organisms includes micro-organisms, bacteria, undulating bacteria, spirochetes, spores, spore-forming organisms, gram-negative organisms, gram-positive organisms, yeasts, fangs, molds, viruses, aerobes, anaerobes, mycobacteria, and the like.

Figure 5:
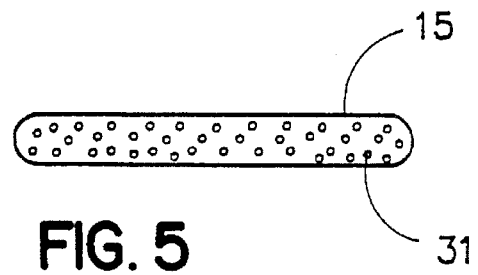
FIG. 5, 6, 7 and 8 depict, in opened view, delivery devices provided by the invention for inserting through the exit port of a urine receiving container into the container for delivering a biocide therein for effecting a substantially germ-free environment inside the container.
Figure 6:
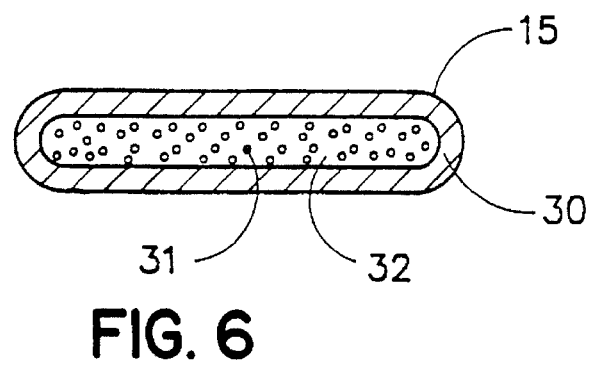
Figure 7:
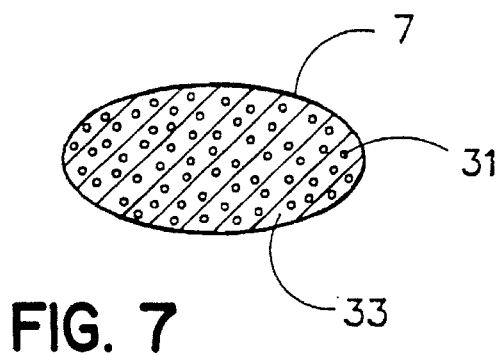
Figure 8:
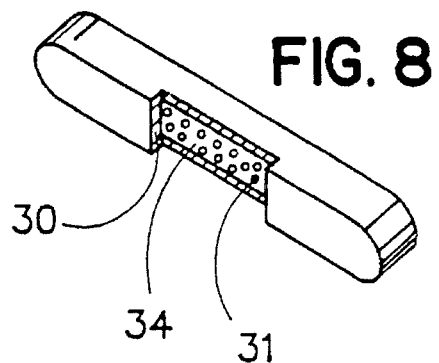

Delivery device 15 comprises a body sized, shaped, and adapted for placement through the exit port of a drainage container into the container. Delivery device 15, in a preferred manufacture, comprises a shape and dimensions that correspond to the shape and dimensions of the exit port. Device 15 comprises at least one surface 28, or device 15 comprises a multiplicity of surfaces 28, 29, for dispensing a biocide from device 15. Device 15 in another preferred embodiment comprises a biocide release rate wall 30, which wall surrounds at least in port, or surrounds totally device 15. The release rate wall 30 meters a biocide, identified by dots 31, from device 15 at a controlled rate of time, over a prolonged period of time from 30 minutes to 336 hours. Device 15 can embrace any preselected geometric shapes, such as square, round rectangle, triangle, crescent, and the like. Device 15 can be manufactured as a rolled film, strip, rod, cylindrical rod, matrix, prism of various cross-sections, such as cruciform, hexagonal, and the like. Device 15 can be seen in FIG. 5 manufactured as an extruded rod comprising a biocide 31; device 15 can be manufactured as seen in FIG. 6 by coextruding a release rate controlling wall 30 that surrounds an internal composition 32 comprising a biocide 31; device 15 is seen in FIG. 7 in cross-section through the body of the device wherein device 15 comprises a matrix 33 comprising a biocide 31; and device 15 is seen in FIG. 8 comprising a wall 30 with a sectioned removed which wall 30 surrounds an internal compartment 34 comprising a biocide 31, which biocide is released over time for destroying or inhibiting the growth of organisms in the urine drainage container.

DETAILED DISCLOSURE OF THE INVENTION

Dispensing device 15 used for the purpose of this invention comprises a polymeric composition, that houses an antimicrobial and permits the release of the antimicrobial into a fluid environment of use. The polymeric composition is permeable to the passage of an antimicrobial and to the passage of fluid. The polymeric composition can be a homopolymer, copolymer, terpolymer, non-cross-linked polymer, cross-linked polymer, diffusion polymer, microporous polymer, and the like. Representative of polymers suitable for forming device 15 include acrylic polymers and copolymers of methylmethacrylate; homopolymers and copolymers of vinyl chloride including vinyl chloride-vinyl acetate copolymer; chlorinated vinyl-chloride; polyethylene; ethylene-propylene copolymer; chlorinated polyethylene; ethylene-vinyl acetate copolymer; styrene-butadiene copolymer; acrylonitrile-styrene-butadiene-terpolymer; polyvinylidene chloride; vinyl-chloride-acrylonitrile copolymer; vinylidene chloride-acrylate ester copolymer; polybutylene terphthalate; vinyl chloride-acrylate ester copolymer; cross-linked polyvinyl acetals such as cross-linked polyvinyl formal; cross-linked polyvinyl butyral; polyethers; sparingly cross-linked polyesters; polyurethanes; chlorosulfonated polyolefins; polyolefins; polyisoprene; polybutadiene; polysilicone; and the like. Exemplary of additional polymers for fabricating the device comprise ethylene-vinyl ester copolymers of the general formula:

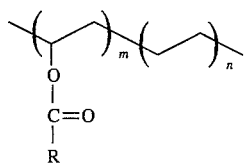

wherein R is hydrogen, lower alkyl of 1 to 7 carbons an aryl, and m is (4 to 80)% by weight and n is (4 to 80)% by weight and n is (100-m)% by weight. Typical alkyl groups include methyl, ethyl, propyl, isopropyl, tert-butyl, pentyl and hexyl. Typical aryl groups include phenyl. Representative ethylene-vinyl ester copolymers, named as the acetates, include ethylene-vinyl formate, ethylene-vinyl acetate, ethylene-vinyl methylacetate, ethylene-vinyl ethylacetate, ethylene-vinyl propylacetate and the like. A preferred ethylene-vinyl ester copolymer includes ethylene-vinyl acetate having a vinyl acetate content of about 4 to 80% by weight of the total, a melt index of about 0.1 to 1000 grams per ten minutes, a density of 0.920 to 1.09, and a frequency of acetoxy groups on the polyethylene backbone of 1/150 to 1/35. Ethylene-vinyl ester copolymers are commercially available and they are described in U.S. Pat. Nos. 2,200,429; 2,396,785 and 2,947,735; and British Pat. Nos. 569,927 and 582,093; and in Crystalline Olefin Polymers, edited by Raff, R. A. V. and Doak, D. W., Part II, pages 261 to 266, 1964, published by Interscience Publishers, New York. Exemplary of a segmented thermoplastic copolyester elastomer consisting essentially of a multiplicity of recurring long chain ester units and short chain ester units joined head-to-tail through ester linkages, the long chain ester units being of the formula:

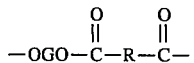

and the short chain ester units being of the formula:

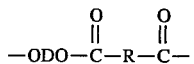

where G is a divalent radical remaining after the removal of terminal hydroxyl groups from a poly(alkylene oxide) glycol having a molecular weight of about 400 to 4000 and a carbon-to-oxygen ratio of about 2.0 to 4.3, R is a divalent radical remaining after removal of carboxyl groups from a dicarboxylic acid having a molecular weight less than about 300, and D is a divalent radical remaining after removal of hydroxyl groups from a diol having a molecular weight less than about 250, provided the short chain ester units constitute about 30% to about 90% by weight of the copolyester, at least about 70% of the radicals represented by D are 1,4-butylene radicals and at least about 70% of the radicals represented by R are 1,4-phenylene radicals, with the sum of the percentages of R radicals which are not 1,4-phenylene radicals and of the D radicals which are not 1,4-butylene radicals not exceeding about 30. The polymers embraced by formula (1) and (2) are commercially available under the trademark Hytrel® polymer. These polymers and methods for preparing them are described in U.S. Pat. Nos. 3,651,014; 3,763,109, and 3,766,146. The disclosure of these patents with respect to the manufacture, composition, and properties of the polymers is incorporated herein by reference. The preferred copolyesters of formula (1) and (2) for use in the invention are those wherein the short chain ester units constitute about 30% to about 60% by weight of the copolyester, G in formula (1) is a poly(alkyleneoxy) radical wherein the alkylene group is of 2 to 4 carbon atoms, all of the D radicals of formula (2) are 1,4-phenylene. Of these preferred copolyesters those wherein G in formula (1) is a poly(tetramethyleneoxy) radical having a molecular weight of 800 to 1200 are particularly preferred for the present purpose. The polymers used herein are disclosed in *Handbook of Common Polymers*, by Scott et al, 1971, published by CRC Press, Cleveland, Ohio; in *Modern Plastics Encyclopedia*, 1979, published by McGraw-Hill Inc., New York, N.Y.; and in *Handbook of Plastics and Elastomers*, by Harper, 1976, published by McGraw-Hill Inc., San Francisco, Calif.

The antimicrobial agent useful for the purpose of the invention include a member selected from the group consisting essentially of a phenol, quaternary ammonium biocides, surfactant biocides, chlorine-containing biocides, quinoline, quinaldinium, lactone, antibiotics, dye, thiosemicarbazone, quinone, sulfa, carbamates, urea, salicylamide, carbanilide, amide, guanide, amidine, imidazoline antimicrobial agents.

Exemplary antimicrobial dyes include acridine, acriflavine, aminacrine hydrochloride, proflavin hemisulfate, triphenylmethane, magenta, crystal violet, scarlet red, pararosaniline, and rosaniline. Exemplary chlorine releasing biocides include sodium hypochlorite, oxychlorosene, chloramine, dichlorodimethylhydantoin, halazone, dichloramine, chlorasine, succinchlorimide, trichloroisocyanuric acid, dichloroisocyanurate, trichloromelamine, dichloroglycoluril, halogenated dialkyl-hydantoin, and halane.

Exemplary antimicrobial quinaldinium and quinoline biocides are dequalinium, laurolinium, hydroxyquinoline, lioquinol, chlorquinaldol and halquinol. Exemplary quaternary ammonium biocides include pyridinium biocides, benzalkonium chloride, cetrimide, benzethonium chloride, cetylpyridinium chloride, chlorphenoctium chloride, cetylpyridinium chloride, chlorphenoctium amsonate, dequalinium acetate, dequalinium chloride, domiphen bromide, laurolinium acetate, methylbenzethonium chloride, myristyl-gamma-picolinium chloride, ortaphonium chloride, and triclobisonium chloride. Exemplary furans include griseofulvin, nitrofurfural, nitrofurazone, nitrofurantoin, furazolidone, and furaltadone.

Exemplary phenol antimicrobial include a member selected from the group consisting essentially of chlorinated phenol, cresol phenol, thymol, chlorocresol, chloroxylenol, hexachlorophane, bisphenols, amylmetacresol, bithionol, chlorothymol, dichloroxylenol chiorophene, p-chlorophenol, p-phenylphenol, trinitrophenol, dichlorobisphenol, and bromochlorobisphenol. Exemplary antibiotics include penicillins, gentemyctin, aminoglycosides, benzylpenicillin, ampicillin, tetracyclines, cephalosporins, neomycin, chloramphenicol, vancomycin, fudicin, rifampicin, cephaloridine, erythromycin, actinomycin, neomycin, polymyxin, colistin, gentamicin, bactriun, carbenicillin and streptomycin, Exemplary lactones include propiolactone. Exemplary urea biocides include noxytiolin, polynoxylen and triclocarbon.

Examples of other antimicrobial useful for the purpose of the invention are chlorhexidine gluconate, chlorhexidine, chlorhexidine acetate, chlorhexidine hydrochloride, dibromopropamide, halogenated diphenylalkanes, cibromsalan, metabromsalan, tribromsalan, carbanilide, salicylanilide, tetrachlorosalicylanilide, trichlorocarbanilide, propamide isethionate, pentamidine, picloxydine, mendalamine, methenamine salts, the acid addition and quaternary, methenamine mandelate, bronopol polyoxmethylene esters such as polyoxmethylene diester, polyoxmethylene diacitate, and the like, and mixtures thereof.

The amount of antimicrobial agent in device 15 generally will be about 0.1% to 80% by weight, with a more preferred amount of 5% to 50% by weight. The device can be manufactured for releasing anti-invective amounts of antimicrobial agent over a prolonged period from several hours to 30 days or longer, with a more preferred period of 30 minutes to 336 hours. Delivery systems that release a biocide for 30 minutes to 720 hours also are provided by the invention for prolonged biocidial activity. The devices of the invention release from 10 mg to 750 mg per hour, or higher. One device can be used at a time, or two or more devices can be used at a time. The devices can be used in succession, and more than one device can be used simultaneously.

The antimicrobial agent kills, prevents or retards the presence of harmful or unwanted micro-organisms inside a urine container. Typical micro-organisms include the fungi *Aspergillus niger, Aspergillus flavus, Rhizopus nigricans, Cladosporium herbarium, Epidermophyton floccosum, Trichophyton mentagrophytes, Histoplasma capsulatum*, and the like. The term, "micro-organisms," also includes *Pseudomonas aeruginosa, Escherichia coli, Proteus vulgaris, Staphyloccus aureus Streptococcus faecalis*, Klebsiella, *Enterobacter aerogenes, Proteus mirabills*, other gram-negative bacteria and other gram-positive bacteria, mycobactin, and the like. The term also embraces yeast such as *Saccharomyces cerevisiae, Canndida albicans*, and the like. Additionally, spores of micro-organisms, viruses and the like, are within the intent of the invention.

The biocides are disclosed in *Disinfection, Sterilization and Preservation*, by Block, (1977), published by Lea & Febiger, Philadelphia, Pa.; in *Inhibition and Destruction of Microbial Cells*, by Hugo, (1971), published by Academic Press, New York, N.Y.; in *Martindale, The Extra Pharmacopoeia*, edited by Blacow, published by The London Pharmaceutical Press, London; and in U.S. Pat. No. 4,445,889.

Those skilled in the art to which this invention pertains can select a polymer for forming a device, and for selecting a wall-forming polymer by measuring the rate of diffusion through a polymeric material. Various techniques can be used to determine the permeability of a homopolymer, copolymer or terpolymer to the passage of a biocide. One method that can be used is to position a film of the polymer, of known thickness, as a barrier between a rapidly stirred, saturated solution of the biocide and a rapidly stirred solvent bath, at a constant temperature, typically 25° C., and periodically measuring the concentration in the biocide solution and in the solvent bath. Then, by plotting the biocide concentration in the solvent bath versus time, the absence of the degree of permeability, P, of the polymeric film is determined by Fick's Law of Diffusion. Fick's Law of Diffusion is expressed by the following equation (1):

$$\text{Slope of plot} = (Q_1 - Q_2/t_1 - t_2) = PAc/h$$

wherein $Q_1$=cumulative amount of drug in solvent in micrograms at $t_1$.

$Q_2$=cumulative amount of drug in solvent in micrograms at $t_2$.

$t_1$=elapsed time to first sample, i.e., Q1

$t_2$=elapsed time to second sample, i.e., Q2

A=area of film in cm

By determining the slope of the plot, i.e., $[Q_1-Q_2/t_1-t_2]$ and solving the equation using the known or measured values of A, C and h, the permeability P constant in $cm^2$/time of the film for a given biocide is readily determined. The procedures used to determined the rate of release through the polymer can be ascertained easily by standard techniques known to the art as recorded in *J. Pharm. Sci.*, Vol. 52, pp 1145–49, (1963); ibid, Vol. 53, pp 798–802 (1964); ibid, Vol. 54, pp 1459–64, (1965); ibid, Vol. 55, pp 840–43 and 1224–39, (1966); *Encyl. Polymer Sci. Technol.*, Vol. 5 and 9, pp 65–82 and 794–807, (1986); the references cited therein, and the like.

The dispensing device of the invention in one embodiment, can be made by blending a polymer and an antimicrobial agent to yield a homogenous composition. The composition can be melt extruded into an preselected shape, such as fiber, rod, and the like. The composition, in another embodiment can be co-extruded with an outer wall forming polymer to provide an antimicrobial release rate wall that surrounds an internal matrix comprising the active antimicrobial agent. The polymeric composition is extruded by a forced flow through a forming die, which die is shaped to produce the required cross-section. Inherent in the extrusion process is the softening, by heat, or optionally, by solvent, of the composition being formed so that it can be conveyed and formed into the desirable final shape. The process takes place with an extruder, a processing machine convention to the plastic industry. The extruder that can be used for the present purpose include a positive displacement, a raw extruder, continuous-flow ram extruder, gear-pump extruder, intermeshing-twin screw extruder, viscous-drug extruder, single stage extruder, screwless extruders, and the like can be extruded into a preselected shape, such as fiber, rod, egg, star, and the like shapes. The composition, in another embodiment, can be co-extruded with an outer wall-forming polymer to provide a release rate wall that surrounds an internal matrix comprising the active antimicrobial agent. The polymeric composition is extruded by a forced flow of the composition through a shape-forming die, which die is shaped to produce the required cross-section. The extrusion process operates by softening the composition, by heat, or optionally by solvent, so the extrudable composition formed can be conveyed and formed into the desired final shape. The process takes place with an extruder, which is a processing machine known to the plastic industry. Representative of extruders that can be used for the present purpose include a positive displacement extruder, a ram extruder, continuous-flow ram extruder, gear-pump extruder, intermeshing-twin screw extruder, viscous-drug extruder, single stage extruder, screwless extruder, and the like. Procedures for operating extruders and extruders are known in the *Encyclopedia of Polymer Science and Technology*, Vol. 8, pp 533 to 587, (1968) published by John Wiley & Sons, New York, N.Y.

DETAILED DISCLOSURE OF EXAMPLES

The following examples well serve to further illustrate the present invention, but the invention is not intended to be limited thereto.

EXAMPLE 1

A dispensing device comprising a rod shape is prepared by blending the antimicrobial agent bronopol with ethylene-vinyl acetate copolymer comprising a vinyl acetate content of 33%, in a high intensity mixer to produce a homogenous blend. The ratio of the antimicrobial agent to the copolymer is 70% bronopol based on 100% weight basis. The composition comprising the antimicrobial and the copolymer were melt extruded to form a dispensing device comprising a rod shape. The rod shape corresponds to shape of the exit port of an urinary drainage container, wherein when the rod is pushed therethrough it dispenser the antimicrobial bronopol for killing the pathogens in the container.

EXAMPLE 2

The above procedure is followed in this example, with the added manufacturing procedure that the rod is surrounded with a wall by co-extruding the composition with an outer wall-forming composition comprising the polymer Hytrel® to yield a wall 5 mil thick. The dispensing device provided by Examples 1 and 2 dispense 25 to 50 µg/ml of antimicrobial bronopol for killing pathogens in a 2000 ml/day urine output into a urine drainage container. The invention provides dispensing device that dispenses from 20 to 80 µg/cm$^2$ hr for controlling pathogens in a urine container receiving 83 ml/hr of urine. The antimicrobial bronopol is chemically known as 2-bromo-2-nitro-1,3-propanediol. The Hytrel® polymer forming the release rate wall is a block copolymer comprising 33% tetramethylene terephthalate and 67% poly(tetramethyl ether) glycol terephthalate. The dispensing device comprising an outer wall surrounding the inner matrix rod exhibited a combined outside diameter of 0.558 cm and a length of 11.1 cm for a total area of 20 cm$^2$. The initial release of bronopol is 245 µg/cm$^2$hr with a steady state release of bronopol of 56 µg/cm$^2$hr. Two such dispensing devices (40 cm$^2$) will provide a biocidal unit amount of bronopol to kill pathogens.

EXAMPLE 3

Following the above Examples, a dispensing device is manufactured with a 0.559 cm diameter as a heat extruded tube having a 0.2 cm bore and a wall thickness of 0.18 cm. The tube is sleeved with a release controlling wall comprising a polymer selected from the group consisting of ethylene-vinyl acetate copolymer, and tetramethylene terephthalate poly(tetramethyl ether) glycol terephthalate copolymer. Accompanying FIG. 8 depicts the release rate for one dispensing device provided by the invention.

EXAMPLE 4

A dispensing device of tubular shape is made as follows: first 45 grams of powdered aminacrine hydrochloride is blended for 10 to 15 minutes at 25° C. on a two-roll mill, with 55 grams of powdered, transparent ethylene-vinyl acetate copolymer having a vinyl acetate content of 28% weight, to produce a film consisting of a homogenous dispersion of the antimicrobial agent in the copolymer. Next, the film is ground in a rotary grinder to produce particles sized 1/16 to 1/2 inches, average size, and the particles then transferred to the hopper of an extruder. The particles were extruded through a tubing die at 60° to 70° C. to yield a dispensing device. The device had an outside diameter of 5 mm, an inside diameter of 2.2 mm and a length of 5 cm. THe dispensing device exhibits a steady-state delivery of an effective amount of antimicrobial over a prolonged period of 24 hours. The device is non-erodible and keeps its integrity during its residency in a urine environment of use.

EXAMPLE 5

A dispensing device for delivering methenamine hydrochloride, an antimicrobial agent, is prepared as follows: first 50 grams of the antimicrobial agent are ground to a powdered state and fed to a two roller mill for blending with an olefin polymer comprising ethylene-vinyl acetate copolymer having a vinyl acetate content of 18% to produce a composition in film shape. The film composition comprising the olefin polymer and the antimicrobial agent is removed from the mill, cut into sections and fed to a coextruder. The coextruder was previously charged with a wall forming butylene terephthalate)-poly-(tetrahydrofuran) copolymer, and the olefin antimicrobial composition as a rod surrounded by the wall forming polymer. The device keeps it integrity in the presence of urine and releases the antimicrobial agent at a controlled rate over a prolonged period of 35 hours.

EXAMPLE 6

The release rate of a dispensing device is measured in a synthetic urine. The synthetic urine is prepared in two separate solutions. One solution comprises dextrose ($C_6H_{12}O_6$), having a concentration of 0.83 g/l, magnesium sulfate ($MgSO_4.H_2O$), having a concentration of 1.54 g/l and urea [$(NH_2)_2CO$] having a concentration of 18.0 g/l. The second solution comprises dipotassium monohydrogen phosphate, $K_2HPO_4$, having a concentration of 4 g/l, disodium monohydrogen phosphate, $Na_2HPO_4.H_2O$, having a concentration of 2.68 g/l, monosodium dihydrogen phosphate, $NaH_2PO_4.H_2O$, having a concentration of 1.62 g/l, sodium citrate, $C_6H_5NaO_7$. $2H_2O$, having a concentration of 1 g/l, sodium chloride, NaCl, having a concentration of 5.3 g/l, and ammonium sulfate, $(NH_4)_2 SO_4$, having a concentration of 1.2 g/l. The first solution is filtered through a 0.2 µm filter. The second solution is autoclaved for 17 minutes at 121° C. and 15 psi pressure. The two solutions are combined after the second solution is cooled to room temperature.

Figure 9:
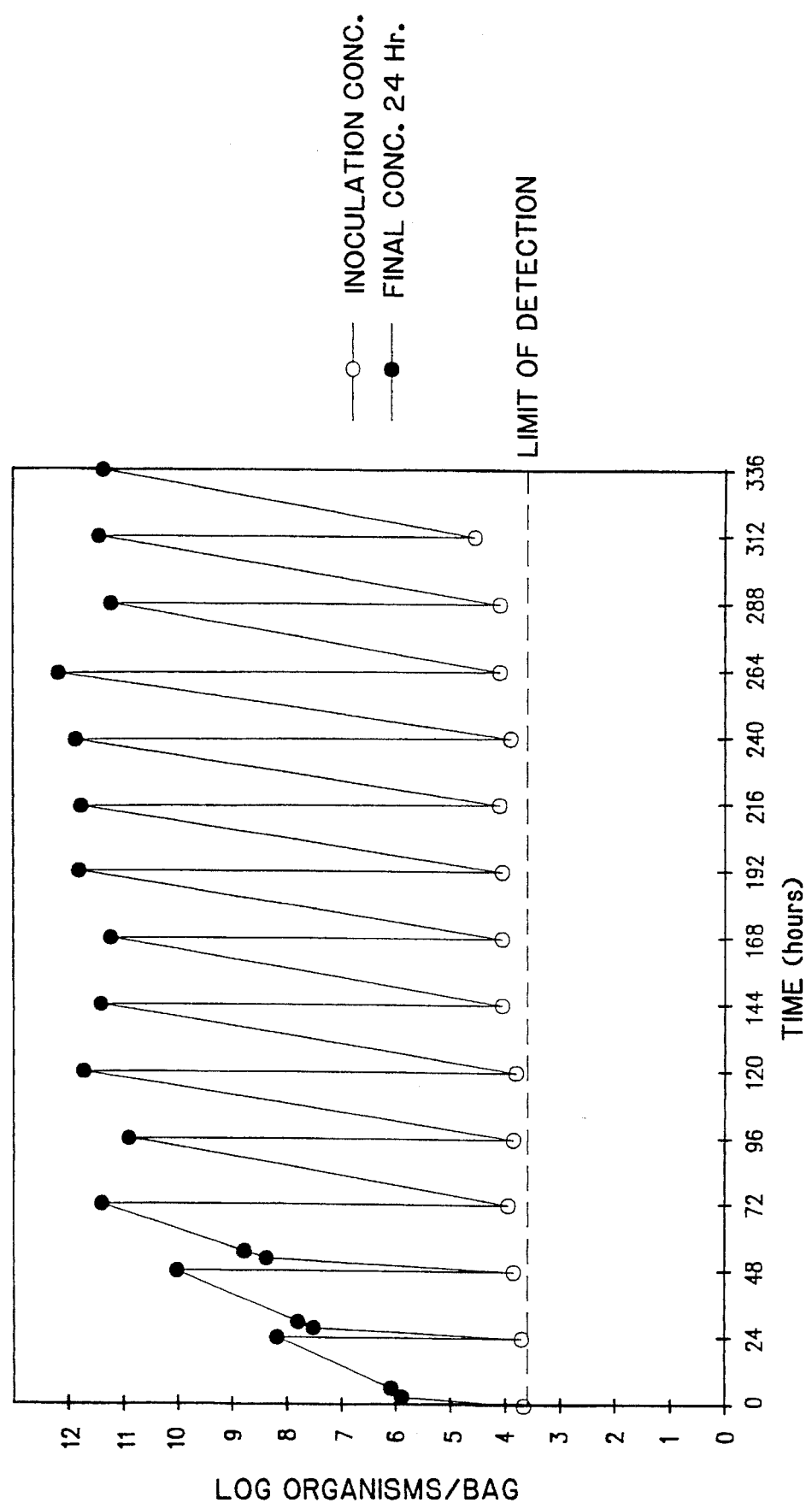
FIG. 9 is a graph that illustrates bacterial growth of *Escherichia coli*, obtained from American Type Culture Collection (ATCC) 8739, in a urine container, or bag, free of an antimicrobial agent.
Figure 10:
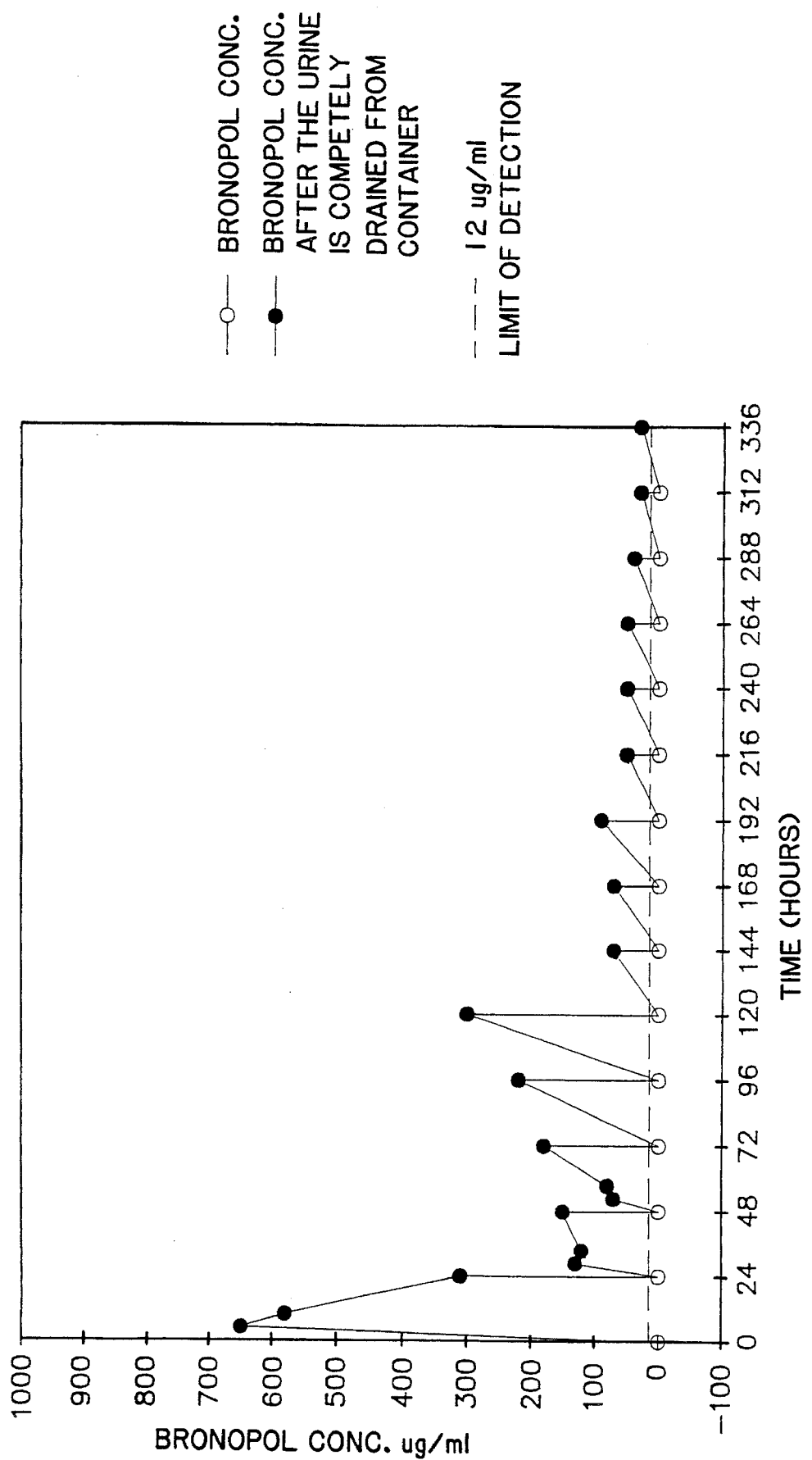
FIG. 10 is a graph that illustrates a biocide concentration in a urine container wherein a delivery device delivers an antimicrobial agent, bronopol.
Figure 11:
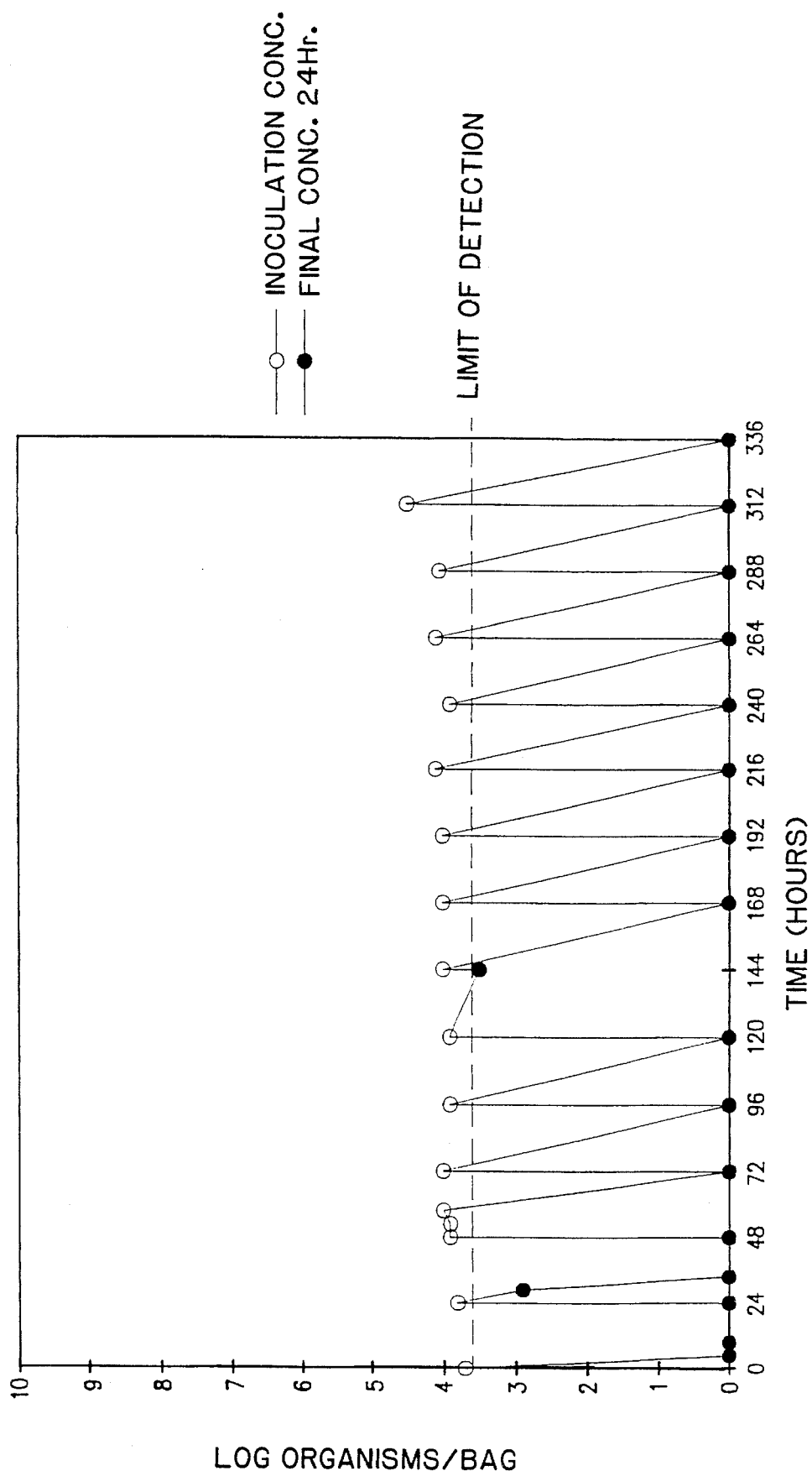
FIG. 11 depicts the results of a disinfectant delivery system, DDS, releasing the antimicrobial bronopol from ethylene vinyl acetate copolymer, EVA, against *Escherichia coli* (ATCC 8739) in a urine bag over 336 hours.

The synthetic urine is pumped into a series of urine drainage containers. The containers were charged at a rate of 75 ml/hr. All the containers received an initial inoculation of *Escherichia coli* at approximately 10$^4$ cells per container. Samples were removed at various periods for analysis. The containers were emptied every 24 hours just prior to reinoculation. A dispensing device comprising ethylene-vinyl acetate copolymer and bronopol and shaped like a flexible rod is inserted through the exit port of a urine drainage container. Accompanying FIG. 9 depicts the microbial growth of *Escherichia coli* in a urine container comprising synthetic urine and free of a delivery device. Accompanying FIG. 10 depicts the concentration of the antimicrobial bronopol, at the end of every 24 hours, in a urine drainage container comprising synthetic urine, free of bacteria, and wherein the delivery device consists of ethylene-vinyl acetate copolymer (EVA) comprising bronopol, 40% bronopol-60% copolymer (40/60), which device was inserted through the exit port of the drainage container. The urine container was emptied every 24 hours prior to being infused with synthetic urine. Accompanying FIG. 11 depicts the concentration of *Escherichia coli* in a urine drainage container containing synthetic urine, and wherein the container comprises a delivery device (DDS) containing bronopol in a matrix comprising ethylene-vinyl acetate copolymer, (EVA 210) wherein the device comprises 40% bronopol to 60% copolymer (40/60).

EXAMPLE 7

Figure 12:
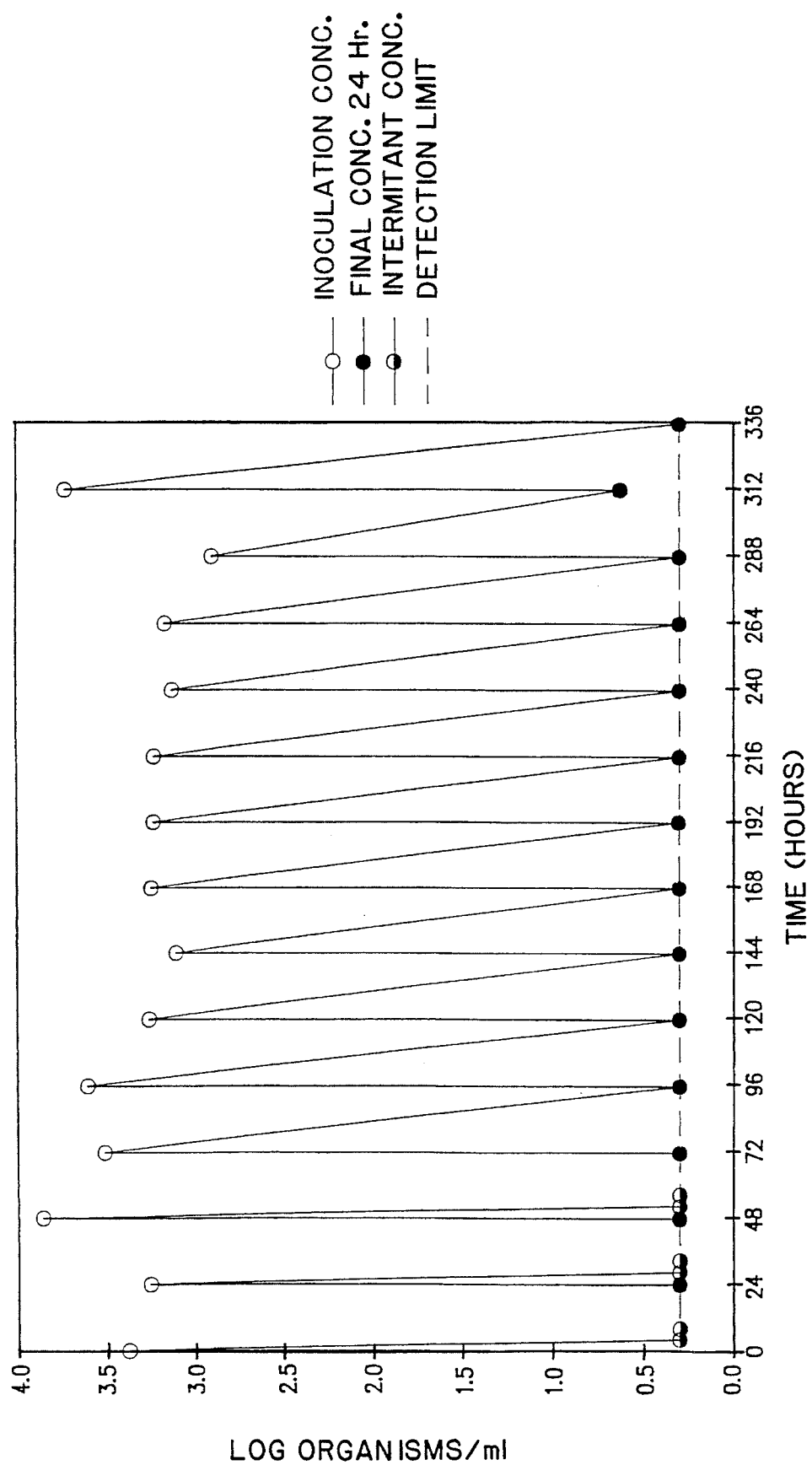
FIG. 12 depicts the results affected by a disinfectant delivery system, DDS, in a urine bag against the bacteria *Pseudomonas aeruginosa* (ATCC 9027) over 336 hours.
Figure 13:
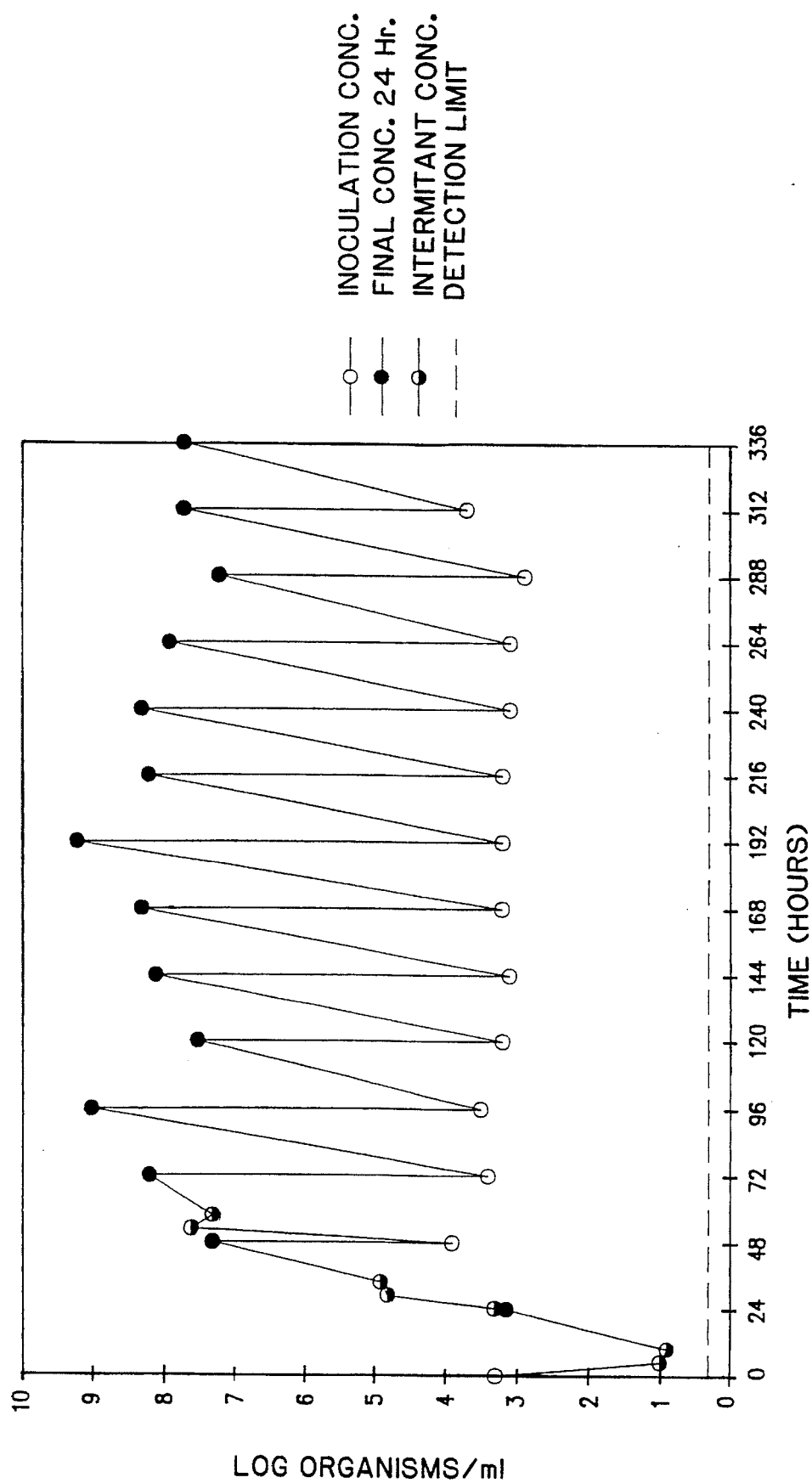
FIG. 13 depicts the microbial growth of *Pseudomonas aeruginosa* (ATCC 9027) in a urine bag that does not contain a disinfectant delivery system, DDS.

The operability and efficiency of an urinary bag disinfectant delivery system (DDS) was demonstrated as follows: first, synthetic urine was infused into urinary bags at a rate of 75 ml/hr. The bags received an initial inoculation of approximately 10$_4$ microorganisms per bag delivered through the exit port into the urinary bags. The bags were drained and reinoculated daily with 10$^3$–10$^4$ microorganisms per bag for two weeks. The DDS was inserted through the exit port into the urine bags, wherein the DDS maintained the synthetic urine sterile for the duration of the test period. In the control bags, bags without DDS, the microorganisms count increased 10$^7$–10$^9$ CFU, colony forming unit, per milliliter after the first 2 to 3 days and maintained that level for the remainder of the test period. Accompanying FIGS. 12 and 13, respectively, depict examples of treated and untreated urinary bags inoculated with microorganisms.

Accompanying FIG. 14 depicts concentration-time profiles in urine bag 1 and urine bag 2, for the disinfectant bronopol in synthetic urine, over a period of more than one month. The steady state disinfectant release rate was determined to be the equivalent to the minimum bactericidal concentration (MBC) of the pathogens evaluated in the study. The DDS used in the studies accompanying FIGS. 12, 13 and 14, comprised a ethylene-vinyl acetate copolymer matrix comprising bronopol with the matrix was surrounded with a wall comprising poly(butylene terephthalate)poly(tetrahydrofuran) block copolymer.

EXAMPLE 8

The above examples are repeated in this example wherein the delivery system is sized, shaped and adopted for pushing through the exit port of a urine bag. The device in the example comprises a matrix of polysilicone surrounded with a release rate wall comprising ethylene-vinyl acetate copolymer. The biocide in the matrix comprises the anti-infective biocide chlorhexidine, methenamine iodobenzylate, methenamine camphorate, methenamine allyl iodide, methenamine hippurate, methenamine hydriodide, or methenamine tetraiodide.

The biocide is dispensed by the device to kill, cleanse, prevent and/or retard the presence or propagation of harmful or unwanted micro-organisms as defined supra. The microorganisms include the fungi *Aspergillus niger, Aspergillus flavus, Rhizopus nigricans, Cladosporium herbarium, Epidermophyton floccosum, Trichophyton mentagrophytes, Histoplasma capsulatum,* and the like the term micro-organisms also includes antibacterial activity against *Pseudomonas aeruginosa, Escherichia coli, Proteus vulgaris, Staphyloccus aureus Streptococcus faecalis,* Klebsiella species, *Enterobacter aerogenes, Proteus mirabills,* other gram-negative bacteria and other gram-positive bacteria, mycobactin and the like. The term also embraces yeast such as *Saccharomyces cerevisiae, Canndida albicans,* and the like. Additionally, spores of micro-organisms, viruses and the like, are within the intent of the invention.

METHOD OF PRACTICING THE INVENTION

The invention concerns also an improvement in a method of using the invention, wherein the method comprises (a) introducing an indwelling catheter into a patient in need of catheterization; (b) connecting the catheter to a urine receiving container; (c) admitting into the urine container through its exit port a device for releasing an antimicrobial agent into fluid present in the container, which agent substantially inhibits the growth of infectious organisms in the fluid, and wherein the improvement in the device comprises: (1) a body sized and shaped for passage through the exit to 30 days in the fluid, said body comprising a polymeric composition an agent into the fluid; (2) an antimicrobial agent in the body in an effective amount for substantially preventing for substantially preventing the growth of organisms in the fluid container; and, (4) releasing the agent from the surface of the device, with the device continually dispensing the antimicrobial agent or a controlled rate in an antimicrobially effective amount into the container for inhibiting the growth of infectious organisms in the container, and concomitantly inhibiting the introduction of infectious organisms into the indwelling catheter, thereby preventing the development of a catheter induced infection in the patient.

It will be understood by those versed in the medico-surgical and patient-care arts, that in the light of the present specification, drawings and the accompanying claims, this invention makes available to the art both a novel and useful combination patient care and a dispensing device endowed with beneficial properties. And, while the invention can be used for collecting all kinds of biological fluids, it will be further understood by those versed in the art that many embodiments of this invention can be made without departing from the scope of the invention. Accordingly, it is to be understood the invention is not to be construed as limited, but it embraces all equivalents inherent herein.

We claim:

1. A method for placing a delivery device comprising an antimicrobial agent into a urine receiving container, said container comprising a wall that surrounds a urine receiving space, an entry port that lets urine into the container, and an exit port distant from the entry port for draining the container; and, wherein said method comprises admitting the delivery device through the exit port into the space for placing the delivery device in the container.

* * * * *